US006545126B1

(12) United States Patent
Johnson et al.

(10) Patent No.: US 6,545,126 B1
(45) Date of Patent: Apr. 8, 2003

(54) CHIMERIC TOXINS

(75) Inventors: Eric A. Johnson, Madison, WI (US); Michael C. Goodnough, Stoughton, WI (US); Carl J. Malizio, Madison, WI (US); Alan B. Scott, San Francisco, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/524,841

(22) Filed: Mar. 14, 2000

Related U.S. Application Data

(60) Provisional application No. 60/125,035, filed on Mar. 18, 1999.

(51) Int. Cl.[7] .................. C07K 14/195; C07K 1/00; C07K 14/33; C07K 14/415; A61K 38/16; A61K 38/46
(52) U.S. Cl. .................. 530/350; 530/370; 514/2; 514/12; 424/94.6
(58) Field of Search ............... 530/350, 370, 530/402; 514/2, 12; 424/94.6; 435/69.7

(56) References Cited

U.S. PATENT DOCUMENTS 6,087,327 A1 * 7/2001 Pearce et al. ............... 514/2

FOREIGN PATENT DOCUMENTS

WO     WO 94/26308     11/1994

OTHER PUBLICATIONS

K.G. Krieglstein, et al., "Covalent Structure of Botulinum Neurotoxin Type A: Location of Sulfhydryl Groups, and Disulfide Bridges and Identification of C–Termini of Light and Heavy Chains," *J. Prot. Chem.* 13(1):49–57, 1994.
J.M. Lord, et al., "Chimeric Proteins Containing Recin A Chain," *Targ. Diag. Ther.* 7:183–190, 1992.
H. Niemann, et al., "Clostridial Neurotoxins: From Toxins to Therapeutic Tools," *Behring Inst. Mitt.* 89:153–162, 1991.
B. Poulain, "Molecular Mechanism of Action of Tetanus Toxin and Botulinum Neurotoxins," *Pathol. Biol.* 42(2):173–182, 1994.
U. Weller, et al., "Cooperative Action of the Light Chain of Tetanus Toxin and the Heavy Chain of Botulinum Toxin Type A on the Transmitter Release of Mammalian Motor Endplates," *Neuro. Let.* 122:132–134, 1991.
G.N. Zercherle, et al., "The Proximity of the C–terminal Domain of *Escherichia coli* Ribosomal Protein L7/L12 to L10 Determined by Cysteine Site–directed Mutagenesis and protein–Protein Cross–linking," *J. Biol. Chem.* 267(9):5889–5896, 1992.

* cited by examiner

*Primary Examiner*—Gabrielle Bugaisky
(74) *Attorney, Agent, or Firm*—Quarles & Brady LLP

(57) ABSTRACT

A chimeric toxin is disclosed. In a preferred embodiment, the chimeric toxin comprises a botulinal neurotoxin heavy chain and non-clostridial toxin chain. A method of creating a chimeric toxin is also disclosed. The chimeric toxin will have utility for pharmacological treatment of neurological disorders.

5 Claims, 6 Drawing Sheets

DTME. Dithio-bis-maleimidoethane
Linker length: 13.3 angstroms
Molecular weight: 312.4

CHIMERIC TOXINS

CROSS-REFERENCE TO RELATED APPLICATIONS

This application claims priority to U.S. provisional application 60/125,035, filed Mar. 18, 1999.

STATEMENT REGARDING FEDERALLY SPONSORED RESEARCH OR DEVELOPMENT

This invention was made with United States government support awarded by the following agencies: USDA Hatch No. 3571. The United States has certain rights in this invention.

BACKGROUND OF THE INVENTION

C. botulinum Toxin Complex

Toxins of the different *C. botulinum* serotypes are produced in culture as aggregates of neurotoxin and other non-toxic proteins non-covalently associated into a polypeptide complex (Schantz, E., Purification and characterization of *C. botulinum* toxins, In K. Lewis and K. Cassel, Jr. (eds.), Botulism. Proceedings of a symposium. U.S. Department of Health, Education, and Welfare, Public Health Service, Cincinnati, pp. 91–104, 1964; Sugii, S. and Sakaguchi, G., *Infect. Immun.* 12:1262–1270, 1975; Kozaki, S., et al., *Jpn. J. Med. Sci. Biol.* 28:70–72, 1974; Miyazaki, S., et al., *Infect. Immun.* 17:395–401, 1977; Kitamura, M., et al., *J. Bacteriol.* 98:1173–1178, 1969; Ohishi and Sakaguchi, *Appl. Environ. Microbiol.* 28:923–928, 1974; Yang, K. and Sugiyama, H., *Appl. Microbiol.* 29:598–603, 1975; Nukina, M., et al., *Zbl. Bakt. Hyg.* 268:220, 1987). Toxin complexes are described as M for medium, L for large and LL for very large. These toxin complexes vary in size from ca. 900 kD for type A LL toxin complex to ca. 300 kD for the type B M complex and type E complex, to 235 kD for type F M complex (Ohishi, I. and Sakaguchi, G., supra, 1974; Kozaki, S., et al., supra, 1974; Kitamura, M., et al., supra, 1969). According to Sugii and Sakaguchi (*J. Food Safety* 1:53–65, 1977), during culture the proportion of one toxin complex versus another is dependent on the growth medium and conditions. A type B culture grown in the presence of 1 mM $Fe^{+2}$ produces an equal proportion of L and M complexes while the same culture grown in the presence of 10 mM $Fe^{+2}$ produces predominantly M complex.

TABLE 1

Molecular sizes of various *C. botulinum* toxin complexes.

| Toxin type | Sedimentation coefficient | ca. M, (kD) |
| --- | --- | --- |
| LL A | 19S | 900 |
| L A, B, D, G | 16S | 450–500 |
| M A, B, $C_1$, D, E, F, G | 10–12S | 235–350 |

Some of the non-toxic proteins associated with the various toxin complexes have hemagglutinating abilities (Sugiyama, H., *Microbiol. Rev.* 44:419–448, 1980; Somers, E. and DasGupta, B., *J. Protein Chem.* 10:415–425, 1991). In particular, non-neurotoxic fractions of the L complexes of type A, B, C, and D have been shown to have hemagglutinating activity. Hemagglutinin fractions isolated from the different serotypes show some serological cross-reactivity. Non-toxic fractions from type A and B serotypes cross-react (Goodnough, M. and Johnson, E., *Appl. Environ. Microbiol.* 59:2339–2342, 1993) as do non-toxic fractions from types E and F. The non-toxic fractions of types $C_1$ and D are antigenically identical as determined by Ouchterlony diffusion (Sakaguchi, G., et al., *Jpn. J. Med. Sci. Biol.* 27:161–170, 1974).

The non-toxic complexing proteins have been demonstrated to be essential for stabilization of the toxin during passage through the digestive tract (Ohishi and Sakaguchi, supra, 1974; Sakaguchi, G., et al., Purification and oral toxicities of *Clostridium botulinum* progenitor toxins, In Biomedical aspects of botulism, G. Lewis (ed.), Academic Press, Inc., New York, pp. 21–34, 1981). Pure neurotoxin has a peroral $LD_{50}$ about 100–10,000 times lower than that of toxin complex on a weight basis (Ohishi, I., *Infect. Immun.* 43:487–490, 1984; Sakaguchi, G., *Pharmacol. Therap.* 19:165–194, 1983). Presumably, the complexing proteins protect the very labile toxin molecule from proteolytic cleavage and other types of inactivation by enzymes, acids and other components present in the gut and circulatory systems since the toxin and the complexing proteins are generally stable in low pH environments.

Analysis by SDS-PAGE has shown that type A toxin complex consists of seven different nontoxic proteins ranging in size from ca. 17 kD to 118 kD in association with a neurotoxic protein of ca. 147 kD (Goodnough, M. and Johnson, E., supra, 1993; Gimenez, J. and DasGupta, B., *J. Protein Chem.* 12:349–361, 1993; DasGupta, *Canad. J. Microbiol.* 26:992–997, 1980). Isolated type A toxin complex has a specific toxicity of $2–4\times10^7$ intraperitoneal $LD_{50}$/mg in 18–22 g white mice. Specific toxicities of other *C. botulinum* toxin complexes are type B M complex—4–5×$10^7$ $LD_{50}$/mg, type $C_1$ M complex—1–2×$10^7$ $LD_{50}$/mg, type D M complex—7–8×$10^7$ $LD_{50}$/mg, type E M complex—1×$10^7$ $LD_{50}$/mg, type F M complex—2–3×$10^7$ LD50/mg (Sugiyama, H., supra, 1980), and 8–9×$10^6$/mg for type G complex (Schiavo, G., et al., *J. Biol. Chem.* 269:20213–20216, 1994).

C. Botulinum Neurotoxin

The biologically active neurotoxin of *C. botulinum* is a dichain molecule of ca. 150 kD in molecular weight. The molecule is composed of two fragments or chains that are termed the heavy chain (Hc, ca. 100 kD) and the light chain (Lc, ca. 50 kD) that are covalently connected by one disulfide bond (FIG. 1). The neurotoxin is synthesized by the organism as a single polypeptide called the protoxin and undergoes post-translational processing termed nicking by at least one protease to generate the two separate chains (Yokosawa, N., et al., *J. Gen. Microbiol.* 132:1981–1988, 1986; Krysinski, E. and Sugiyama, H., *Appl. Environ. Microbiol.* 41:675–678, 1981). The two chains are covalently bound through a disulfide bridge. The nicking event occurs in the culture fluid for proteolytic *C. botulinum* and through the activity of an added exogenous enzyme such as trypsin in non-proteolytic strains (Yokosawa, N., et al., supra, 1986; DasGupta, B., *J. Physiol.* (Paris) 84:220–228, 1990; Kozaki, S., et al., *FEMS Microbiol. Lett.* 27:149–154, 1985).

Functional Domains of Botulinal Neurotoxin

Binding to cell surface. The carboxyl terminus of botulinal heavy chain is responsible for receptor binding on the cell surface. Initial work done using tetanus toxin, which is very similar in structure to botulinum neurotoxin, showed binding to cell receptors involved a multiple step binding sequence. The ten C-terminal amino acids are essential for initial receptor recognition on the motor neuron via a low affinity binding site while a sequence in the middle of the heavy chain was responsible for higher affinity secondary binding through a different protein receptor (Halpern, J. and Loftus, A., *J. Biol. Chem.* 268:11188–11192, 1993).

Evidence shows that binding by type B botulinum neurotoxin occurs in a similar fashion (Nishiki, T., et al., *J. Biol. Chem.* 269:10498–10503, 1994). The initial binding of type B neurotoxin to synaptosomes has been shown to be related to the presence of sialic acid containing motor neuron membrane components such as gangliosides $G_{DIa}$, and $G_{T1b}$ as well as a partially purified 58 kD protein that has been tentatively determined to be a synaptogamin isoform. There is minimal binding of the neurotoxin to the 58 kD high affinity receptor in the absence of the low affinity gangliosides. This indicates that the initial low affinity binding to gangliosides which are prevalent on the cell surface by the carboxyl-terminal amino acids is followed by a high affinity binding to the 58 kD protein by an undetermined region that is located more towards the amino terminus and possibly in the central portion of the heavy chain. Treatment of synaptosomes with proteases and or sialidase decreased binding of the neurotoxin to the synaptosomes.

Channel formation. Once the neurotoxin is bound to the motor neuron via the C-terminus end of the heavy chain, the light chain and the N-terminus of the heavy chain are endocytosed. The proteolytically active light chain is then released into the cytosol of the cell via a translocation event through the phospholipid vesicle membrane. This translocation event is driven by a sequence of amino acids contained in the N-terminal portion of the heavy chain. The predicted sequence responsible for translocation of botulinum toxin type A is from amino acids 650–681 and shows strong sequence homology to tetanus toxin amino acids 659–690 (Montal, M., et al., *FEBS. Lett.* 313:12–18, 1992). Both of these regions contain a high number of hydrophobic amino acid residues which presumably facilitate intercalation into lipid bilayers.

Under the acidic conditions of the vesicle, channels form in the lipid bilayer due to the N-terminal portion of the heavy chain associating into a bundle of amphipathic alpha-helices. These bundles contain four heavy chain portions that allow the light chain to enter the cytosol as evidenced by conformational energy calculations and direct visualization (Montal, M., et al., supra, 1992; Schmid, M., et al., *Nature* 364:827–830, 1993). There are believed to be two different conformations of the channel which may begin forming soon after binding of the C-terminal portion of the heavy chain. One conformation is a low conducting version while the second has a much greater conductance in electrochemical studies (Donovan, J. and Middlebrook, J., *Biochem.* 25:2872–2876, 1986). The difference in the two conformations can be explained by the fact that there is a change in pH from the physiologic condition under which the toxin initially binds and conductance is low to the lower pH values of the endocytotic vesicle where conductance is higher. The rate of conductance through channels has been shown to be highest at a pH of about 6.1 and lower at pH values closer to neutral (Donovan, J. and Middlebrook, J., supra, 1986).

Enzymatic activity in neuron/specificity for substrate. In order to describe the mechanism of botulinum neurotoxins in general, the synaptic vesicle docking cascade must be understood for it is the inhibition of the release of the neurotransmitter acetylcholine from cholinergic motor neurons which leads to the classic flaccid paralysis seen in botulinum-intoxicated muscle tissue.

The key event in the release of neurotransmitter is exocytosis of the synaptic vesicle contents through fusion of the synaptic vesicles with the phospholipid/protein-containing plasma membrane. Normally, synaptic vesicles are pre-docked on the inside of the plasma membrane through a series of docking proteins and acetylcholine molecules are exocytotically released by an increase in the intracellular $Ca^{+2}$ concentration (Südhof, T., *Nature* 375:645–653, 1995). The docking proteins and their relationship to the synaptic vesicles is shown in Table 2.

The neurotoxic activity of all seven serotypes of neurotoxin is related to the fact that the light chains of botulinum toxin as well as the light chain of tetanus toxin are known to be zinc endopeptidases. The zinc binding region of the light chain of the neurotoxins is highly conserved and is very homologous among the different serotypes. It includes a region that possesses the zinc binding motif HExxH surrounded by sequences that show a lesser degree of homology. The intracellular target for each serotype is one or more of the proteins involved in docking of the acetylcholine containing vesicles to the neuronal membrane. Cleavage of the various neurotoxin substrates inhibits the docking of the vesicles with the plasma membrane and, hence, the release of the neurotransmitter into the synaptic junction. The various substrates for the seven serotypes of botulinum neurotoxin as well as tetanus toxin are shown in Table 2.

TABLE 2

Intracellular substrates of clostridial neurotoxins (adapted from Oguma, K. et al., Microbiol. Immunol. 39: 161–168, 1995).

| Neurotoxin serotype | Intracellular target | Cleavage site |
| --- | --- | --- |
| A | SNAP-25 | Gln197—Arg198 |
| B | Synaptobrevin-2 (VAMP-2) | Glu76—Phe77 |
| $C_1$ | Syntaxin (also SNAP-25) | near C-terminus |
| D | Synaptobrevin-1 (VAMP-1) | |
| | Synaptobrevin-2 (VAMP-2) | Lys61—Leu62 Lys59—Leu60 |
| E | SNAP-25 | Arg180—Ile181 |
| F | Synaptobrevin-1 (VAMP-1) | |
| | Synaptobrevin-2 (VAMP-2) | Gln60—Lys61 |
| G | Synaptobrevin-1 (VAMP-1) | Gln58—Lys59 Ala83—Ala84 |
| | Synaptobrevin-2 (VAMP-2) | Ala81—Ala82 |
| Tetanus toxin | Synaptobrevin-2 | Glu76—Phe77 |

Because patients have developed immunity to treatment with type A botulinal toxin complex (Borodic, G., et al., *Neurology* 46:26–29, 1996), a toxin preparation that avoids that immunological problem is highly desired.

Chimeric and Hybrid Toxins

Arnon, et al. (U.S. Pat. No. 5,562,907) has described botulinum toxins combining the heavy and light chain of different botulinum toxin molecules. Weller, et al. (*Neurosci. Letters* 122:132–134, 1991) describes toxins comprising the light chain of tetanus toxin and the heavy chain of botulinum toxin type A.

BRIEF SUMMARY OF THE INVENTION

In one embodiment, the present invention is a chimeric toxin comprising a botulinal neurotoxin heavy chain and a non-clostridial toxin chain, preferably covalently bonded. In one preferred embodiment of the present invention, the non-clostridial-toxin chain is the ricin A chain. In another preferred embodiment of the present invention, the botulinal neurotoxin heavy chain is botulinum toxin type A heavy chain.

Preferably, the covalent bond is a reducible disulfide linker, preferably the linker described in FIG. 2. Alternatively, it is a nonreducible covalent linker, preferably the linker described in FIG. 1.

In a preferred form of the invention, the toxicity is at least $3.0\times10^3$ mouse intraperitoneal $LD_{50}$/mg protein. More preferably, the toxicity is at least $3.3\times10^4$ mouse intraperitoneal $LD_{50}$/mg protein. Most preferably, the toxicity is at least $6.6\times10^4$ mouse intraperitoneal $LD_{50}$/mg protein.

In another embodiment, the present invention is a method of creating a chimeric toxin. The method comprises isolating a botulinum toxin heavy chain and alkylating the free sulfhydryl residues of the chain and then conjugating a non-clostridial toxin chain to the alkylated botulinum heavy chain. Preferably, the alkylation of free sulfhydryl residues is via iodoacetamide.

It is an advantage of the present invention that targeted toxins are developed as reagents for treatment of muscle disorders.

It is another advantage that toxins with an increase in the duration of action is created. Therefore, the treatment is less burdensome for the patient because the patient does not have to be treated as frequently. Current therapy requires frequent exposure of the patient to the toxins and higher incidence of side effects, such as ptosis, and increase in antigen load, which could lead to immunity. The current invention provides durable therapy with fewer side effects. The therapy of the current invention is preferably long-lasting and permanent.

It is another advantage that a toxin with toxicity levels of greater than $3.3\times10^4$ and preferably $6.6\times10^3$ mouse intraperitoneal $LD_{50}$/mg is created, which enables injection of low concentrations thus avoiding side effects and systemic reactions.

Other advantages, features and objects of the present invention will be apparent to one of skill in the art after review of the specification, claims and drawings.

BRIEF DESCRIPTION OF THE SEVERAL VIEWS OF THE DRAWINGS

FIG. 3 describes botulinum toxin type A chain separation following alkylation of free sulfhydryl residues via iodoacetamide.

DETAILED DESCRIPTION OF THE INVENTION

Although botulinum toxin has long been known to be useful in ophthalmic and neurologic clinical practice for therapy of involuntary muscle movements, pain, spasticity and other neuralogic disorders, there are certain drawbacks to its use. One of the most serious drawbacks is a patient's development of only temporary relief and subsequent requirement for periodic injections. The present invention seeks to address some of the drawbacks by providing chimeric botulinal toxins in which the heavy chain of botulinum toxin is conjugated to toxins that lead to neuronal cell death, thereby increasing duration of action.

In practice, injection of a chimeric toxin of the present invention will result in binding to the nerve and incorporation of a lethal toxin into the nerve. Preferably, the nerve cell will be killed. The primary advantage over existing botulinum toxin therapy is increase in the duration of action.

Figure 2:
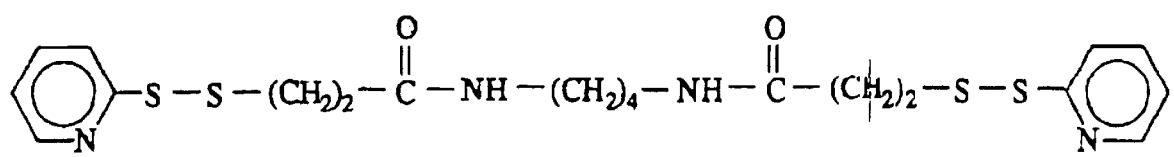
FIG. 2 is a reducible disulfide linker.

In one embodiment, the present invention is a chimeric toxin comprising a botulinum toxin heavy chain covalently connected to a non-clostridial toxin. In a preferred form of the invention, the chimeric toxin comprises the heavy chain of botulinum toxin type A covalently connected with ricin A chain via the reducible linker described in FIG. 2.

Typically, the chimeric toxin of the present invention could be produced by molecular biology techniques wherein the enzymatic (non-botulinal) toxin is encoded by DNA that is placed upstream of the codons encoding the botulinal heavy chain on a high copy number plasmid, the expression of which is under the control of an inducible promoter. There may be some difficulties in making these constructs in *E. coli* in a form in which the expressed produced is biologically active. One difficulty we have encountered is that the gene for type A heavy chain is very A+T rich (up to 90% is some regions) making it difficult to express the gene in organisms such as *E. coli*, which typically have a much lower A+T content (40–50%). One reason that the high A+T gene is not expressed in *E. coli* is that the tRNAs responsible for coding the amino acids such as Ile and Leu (high A+T content in the bot gene) are very rare in *E. coli*. Consequently, when the ribosome goes along the mRNA and encounters one or more of these rare codons (the ribosome stops when it can not find any of the correct tRNSs. This allows the ribosome enough time to dissociate from the mRNA and results in truncated or abbreviated proteins as opposed to full-length transcripts. There is enough flexibility or wobble in the genetic code that the high A+T codons are not used much in *E. coli* which is what allows it to survive. We propose solving this problem by using a non-toxigenic derivative of *C. botulinum* that has had the entire toxin gene cluster deleted.

Suitable Botulinum Toxins

We envision that heavy chains isolated from many different botulinum toxins would be suitable for the present invention. The botulinum heavy chain is responsible for targeting and internalization of botulinum toxin light chain into peripheral nerves. Preferably, the heavy chain is isolated from botulinum toxin type A. However, heavy chains isolated from any of the toxins listed in Table 2, above, would be suitable.

One would choose the appropriate heavy chain by the a variety of criteria. One important criteria is ease of purification, and that is why we have chosen the botulinum toxin type A heavy chain. However, other heavy chains may give the chimeric toxin advantageous properties.

One would preferably obtain botulinum toxin heavy chains as described below in the examples and in FIG. 3. Purification is slightly different for individual serotypes.

Suitable Non-Clostridial Toxins

Preferred Non-clostridial toxins include:

i. ADP-ribosylating toxins, such as brefeldin (*Eupenicillium brefeldianum*), cholera toxin (*Vibrio cholerae*), diphtheria toxin (*Corynebacterium diphtheriae*), pertussis toxin (*Bordetella pertussis*), and other toxins in this family.

ii. Neurotoxins, such as agatoxin (*Agelenopsis aperta*), agitoxin (*Leiurus quinquestriatus herbraeus*), apamin (bee venom), brevetoxin (*Plychodiscus brevis*), alpha-bungarotoxin, beta-bungarotoxin (*Bungarus multicinctus*), calcicludine (*Dendroaspis angusticeps*), cardiotoxins I–IV (*Naja naja atra*), charybdotoxin agitoxin (*Leiurus quinquestriatus herbraeus*), cobra venoms (*Naja naja*), conotoxin (*Conus geographus* and *Conus striatus*), crotoxin (*Crotalus durissus terrificus*), dendrotoxin (*Dendroaspis angusticeps*), Iberiotoxin (*Buthus tamulus*), Kailotoxin (*Androctonus mauretanicus*), Latrotoxin (*Latrodectus tredecimguttatus*), Maitotoxin (*Gambierdiscus toxicus*), Myotoxin (*Crotalus viridis viridis*), Neosaxitoxin (*Gymnodiunium catenatum*), Notexin (*Notechis scutatus*), Okadaic acid (*Porocentrum concavum*), Palytoxin (*Palythoa caribaeorum*), Picrotoxin (*Anamirta cocculin*), Resiniferatoxin (*Euphorbia poisonii*), Saxitoxin (Gonyaulax sps.), Stichodactyla toxin (*Stichodactyla helianthus*), and Tetrodotoxin (Fugu sps.).

iii. Adenylate cyclase activators, such as forkolin (*Coleus forskohlii*).

iv. Pore forming toxins such as streptolysin O, Staphylococcal alpha-toxin, Pneumolysin, *E. coli* hemolysin, aerolysin.

v. Ribosome inactivating proteins (RIPS), including both type I and type II ribosome inactivating proteins. RIPS existing as single chain proteins or glycoproteins are classified as type I RIPS while those that exist as dichain proteins consisting of an A chain have enzymatic activity and a B chain having cell binding properties (particularly those cells showing carbohydrate residues on their surface) are designated type II RIPS. A partial list of some of the RIPS found in nature follows.

| Plant RIPS. | |
| --- | --- |
| Type I | Type II |
| Pokeweed antiviral proteins | Ricin |
| Tritin | Abrin |
| Gelonin | Modecin |
| Momordin | Viscumin |
| Saporin | Volkensin |
| Dianthin | |
| Maize RIP | |
| Bacterial RIPS. | |
| Shiga toxin | (*Shigella dysenteriae*) |
| Shiga like toxin | (certain *E. coli* strains) |
| Fungal RIPS. | |
| alpha-sarcin | (*Aspergillus giganteus*) |
| mitogillin | (*Aspergillus restrictus*) |
| restrictocin | (*Aspergillus restrictus*) |

The purpose of the non-clostridial toxin is neuronal cell death. Therefore, we envision that a variety of toxins would be suitable. We especially envision toxins that would give an increase in duration of therapeutic effect.

A preferred toxin of the present invention is the ricin A chain. Ricin consists of a dichain structure comprising an A chain of 30–32 kD covalently linked to a B chain of 34 kD via a disulfide bond. Following binding to susceptible cells by the B chain of ricin, the A chain is internalized into the cytosol where it irreversibly inactivates the mammalian 28S ribosome by cleaving a single N-glycosidic bond between adenine 4324 and the ribose-phosphate backbone.

Suitable Linkers

Figure 1:
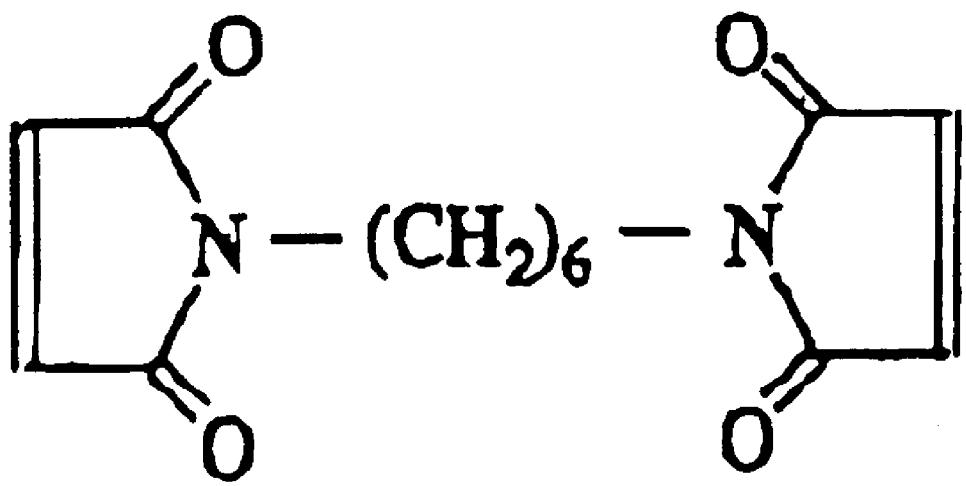
FIG. 1 is a non-reducible straight alkyl chain linker useful in the present invention.

In a preferable form of the present invention, the two toxin chains are connected by a covalent bond. Therefore, after one has obtained both the botulinal and the non-clostridial toxins, one must then link the botulinum and non-clostridial toxins together with retention of biological activity. The Examples below and FIGS. 1 and 2 describe preferable linkers and methods to accomplish functional linkage.

Figure 3:
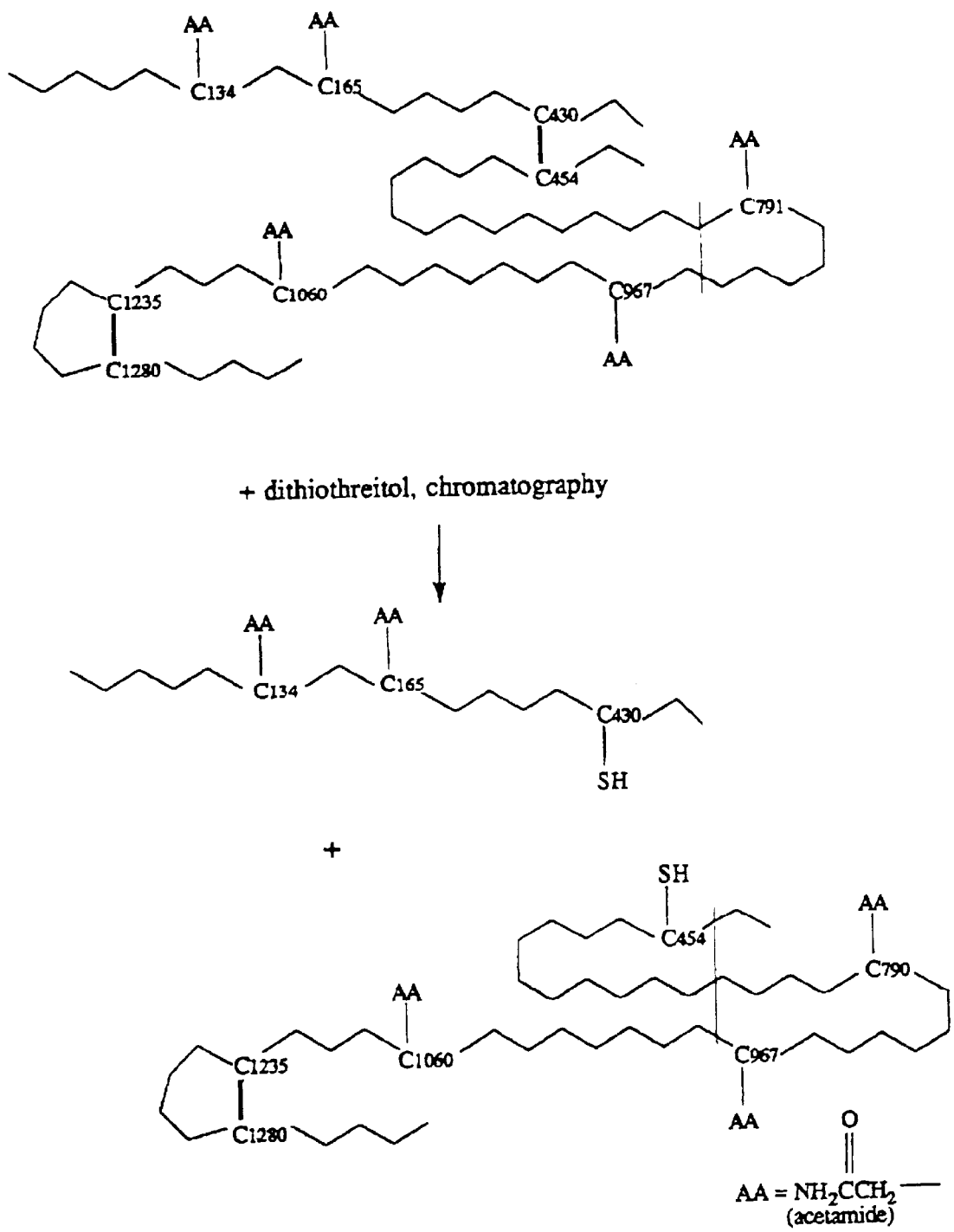
FIG. 3 is a schematic diagram of a portion of the chemical strategy used to create specific chimeras.
Figure 4:
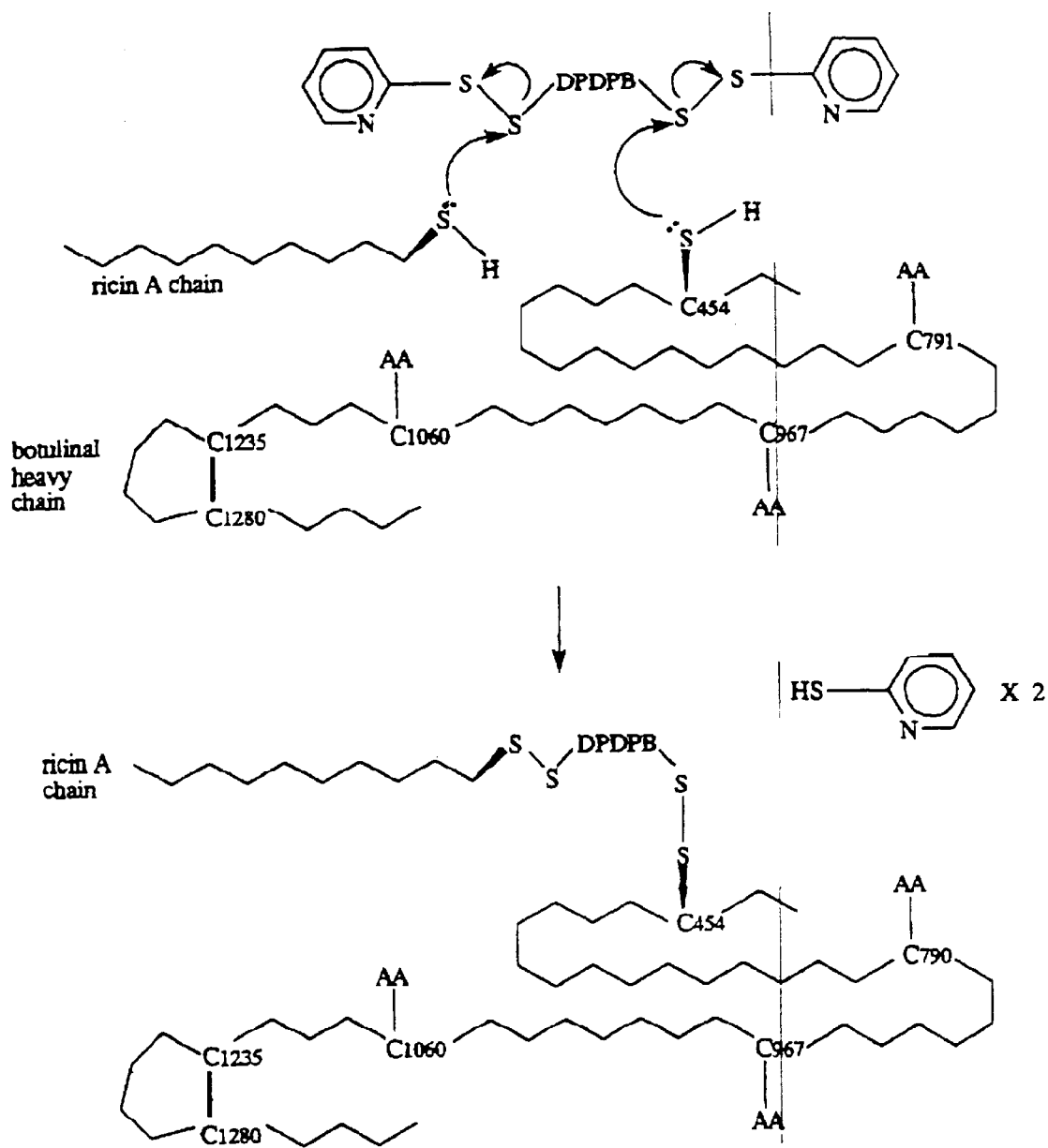
FIG. 4 is a schematic diagram describing the conjugation of ricin A chain to alkylated type A botulinal heavy chain using a linker similar to that described in FIG. 2.

The preferred chemical strategy used to create these specific chimeras is outlined in FIGS. 3 and 4. Our general idea was to target the sulfhydryl group of the botulinal heavy chain originally involved in the disulfide linkage with the botulinal light chain. By chemically blocking the free sulfhydryls on the neurotoxin prior to separation of the two chains, a single reactive sulfhydryl remained on the heavy chain following chain separation. This avoids mixed disulfide linkage and formation of chimeric constructs with no or very low biological activity.

Figure 5:
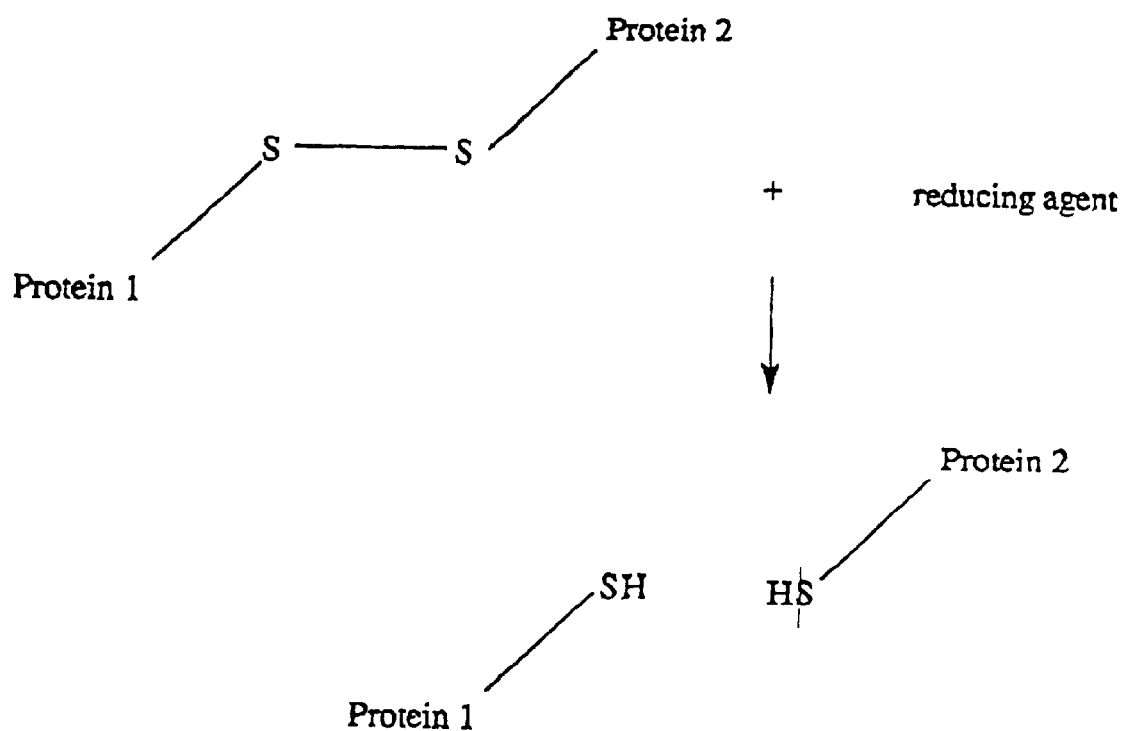
FIG. 5 is a schematic diagram describing the generation of free sulfhydryl groups.

Conjugation reagents contain at least two reactive groups. Homobifunctional cross-linkers contain two or more identical leaving groups while heterobifunctional cross-linkers contain two or more different leaving groups. Linkers that are reactive with sulfhydryl groups on proteins may do so by generating a reducible disulfide linkage or by generating a non-reducible thioether bond. Common reducing agents for reduction of disulfide bonds including those generated with reducible linkers include dithiothreitol, mercaptoethanol, and reduced glutathione. These agents react with disulfide bonds generating two free sulfhydryl groups per original disulfide bond. The chemical reaction is shown in FIG. 5.

We envision that the non-clostridial toxin will be attached via a disulfide bond. For example, ricin A chain has a single free sulfhydryl which made the use of homobifunctional linkers that are reactive with free thiols the logical choice for specific conjugation of the heterologous chains.

Suitable Toxicities

Table 3, in the Examples below, describes the toxicity of preferred final chimeric toxins. Toxins of the present invention have a toxicity of at least $3 \times 10^3$ mouse intraperitoneal $LD_{50}$/mg of protein. Preferably, the toxicity is at least $3.3 \times 10^4$ and most preferably at least $6.6 \times 10^4$ mouse intraperitoneal $LD_{50}$/mg of protein.

Preferable in vivo toxin assays are described below using the method of Schantz and Kautter (1978).

EXAMPLES

1. In General

We have synthesized two different chimeras that differ in the linker used to conjugate the heterologous chains. One linker (BMH [bismaleimidohexane], FIG. 1) is a non-reducible straight alkyl chain while the second (DPDPB [1,4-di-[(3',2'-pyridyl-dithio-(propionamido) butane], FIG. 2) is a reducible disulfide linkage similar to the intact neurotoxin. Both of the linkers are homobifunctional reacting primarily with sulfhydryl groups only under the conditions employed.

The specific toxicities of the chimeric toxins we created are lower than botulinal neurotoxin or ricin holotoxins but are higher than the toxicities of the separate chains for either toxin chain preparation. The non-reducible chimera had a specific toxicity between 2,900 and 5,800 mouse i.p. $LD_{50}$/mg while the reducible chimera had a specific toxicity between 33,000 and 66,000 i.p. $LD_{50}$/mg. The specific toxicity of the type A heavy chain preparation was between 10 and 100 i.p. $LD_{50}$/mg while the ricin A chain had a specific toxicity of <5 i.p. $LD_{50}$/mg. Concentrations of the two chimeras are 56 $\mu$g/ml for the non-reducible and 38 $\mu$g/ml for the reducible. This low residual toxicity could be avoided by using cloned genes for the fragments and expression in a suitable expression system (such as Bradshaw, et al., *Plasmid* 40:233–237, 1998).

We isolated approximately 760 $\mu$g of the reducible toxin and 610 $\mu$g of the non-reducible toxin.

In an effort to reduce the possibility that the toxicity of the chimeras was due to any residual botulinal neurotoxin reformed during the linker addition, both of the preparations were chromatographed on Blue Sepharose. This matrix consists of Cibacron Blue dye bound to agarose. Cibacron Blue is a dye molecule which closely resembles a dinucleotide in structure. Ricin A chain binds to this dye under physiologic conditions while botulinal neurotoxin does not. Toxicity of material which bound to this matrix was due to the chimera alone since any neurotoxin reformed during conjugation of the two heterologous chains was removed during this chromatography and the ricin A chain preparation was essentially non-toxic. Other purification methods could be employed by remove contaminating holotoxin or unreacted chains.

2. Materials and Methods

Bacterial cultures and neurotoxin purification. The Hall strain of type A *Clostridium botulinum* was used for production of type A neurotoxin according to the methods of Goodnough and Johnson (*Appl. Environ. Microbiol.* 58(10):3426–3428, 1992), Goodnough and Johnson (*ACS Symposium Series* No. 567, J. Cleland and R. Langer (eds.), 1994), and Tse, et al. (*Eur. J. Biochem.* 122:493–500, 1982). The neurotoxin was purified according to Goodnough and Johnson and Tse, et al.

Neurotoxin modification and thiol quantitation. Type A neurotoxin was modified by treatment with iodoacetamide (Sigma Chemical Co., St. Louis, Mo.) according to the method of Schiavo, et al. (1990) to block fee sulfhydryls that interfere with subsequent biochemical reactions. By blocking free sulfhydryl residues with IAA prior to reduction of the disulfide bond connecting the botulinal heavy and light chains during separation and purification of botulinal heavy chain, the resulting heavy chain has a single free sulfhydryl residue—namely, the one originally involved in the disulfide bond originally connecting the heavy and light chains in native toxin. The degree of modification was monitored by titration of free thiol using the method of Ellman (1959) as modified by Schiavo, et al. (1990).

Type A neurotoxin heavy chain purification. The botulinal heavy chain of the modified neurotoxin was separated from the catalytic light chain by two chromatographic steps (FIG. 3) essentially by the heavy chain of type A neurotoxin were purified by the method of Sathyamoorthy and DesGupta (1985). Briefly, purified type A neurotoxin was dissolved in 20 mM sodium borate, 40 mM sodium phosphate, pH 8.4, and dialyzed against the same buffer overnight. Approximately, 15 mg of the dialyzed neurotoxin was applied to a column of QAE-Sephadex (1.6 cm×10 cm, Pharmacia) equilibrated with the pH 8.4 buffer at 4° C. After washing with 5 column volumes of loading buffer, the column was washed with one-half column volumes of loading buffer containing 10 mM dithiothreitol (DTT) as a reducing agent followed by a wash with one-half the column volume of loading buffer containing 100 mM DTT plus 2 M urea. The flow was stopped overnight (16 hours) and resumed the following morning with loading buffer containing 10 mM DTT plus 2 M urea. The light chain eluted at this point. Heavy chain was recovered by elution with loading buffer containing 10 mM DTT, 2 M urea, and 200 mM sodium chloride. Heavy chain thus eluted contained a small portion of unnicked neurotoxin (<2%).

Type A heavy chain was further purified by dialyzing fractions from the QAE column against 20 mM sodium phosphate, 5 mM DTT, pH 7.5, followed by chromatography on DEAE-Sephadex (1.6×10 cm) equilibrated with the same buffer. Contaminating light chain was eluted by washing the column with 5–8 column volumes of loading buffer and the heavy chain separated from the residual unnicked neurotoxin with 50 ml of a linear 0–0.12 M sodium chloride gradient followed by a second linear gradient of 150 ml of 0.12–0.6 M sodium chloride. Specific toxicities of heavy chain preparations were between 10 and 100 i.p. $LD_{50}$/mg and were judged to be >95% homogeneous.

Ricin A chain. Ricin A chain was purchased from Sigma Chemical Co. It had a specific toxicity of <5 i.p. $LD_{50}$/mg.

Homobifunctional linkers. The two linkers used in the construction of the chimeric toxins in this work, bismaleimidohexane (BMH, FIG. 1), and (1,4-di[3'-(2'-pyridyldithio)-propionamido)]butane] (DPDPB, FIG. 2), were purchased from Pierce Biochemical, Rockford, Ill. BMH forms a non-reducible thioether linkage between two thiol groups while DPDPB forms two reducible disulfide linkages between different thiols.

Figure 6:
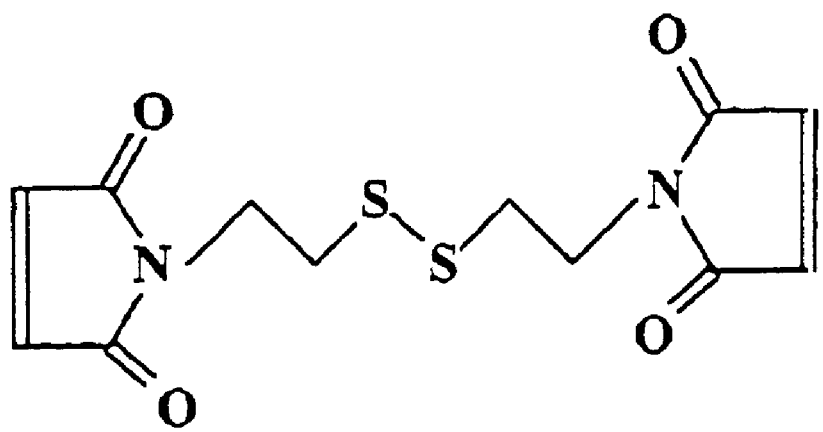
FIG. 6 is a diagram of a dithio-bis-maleimidoethane.

An additional homobifunctional linker has been found to be very useful in conjugation of heterologous proteins including separated botulinal neurotoxin chains and ricin A chain. Dithio-bis-maleimidoethan (FIG. 6) is an intermediate-length, sulfhydryl reactive, reducible linker. The linker reacts with free thiol groups on proteins at pH values of 6.5–7.5 forming stable tioether linkages. In recent work involing reconstitution of botulinal neurotoxin from separated chains from different serotyes, the linker appears to be more reactive with thiols on these chains than DPDPB. The linker also has the requisite reducible disulfide bond needed for full potentiation of the toxins.

Electrophoresis and immunoblotting. Protein samples were examined electrophoretically using the Pharmacia Phastsystem (Pharmacia LKB Inc., Piscataway, N.J.) according to the manufacturers instructions. Precast 12.5% acrylamide and 10–15% gradient acrylamide gels (Pharmacia) were stained with 0.1% coomassie brilliant blue R250 in 16.7% acetic acid, 41.7% methanol. Gels were destained in 7.5% acetic acid, 25% methanol. Samples for electrophoresis were solubilized in 50 mM Tris-HCl, 5 M urea, 5% SDS, 20% glycerol, pH 6.8. Some samples were reduced by addition of dithiothreitol to a final concentration of 0.5%. All samples for SDS-PAGE were boiled for ≧25 minutes prior to electrophoresis. Protein bands from SDS-PAGE gels for analysis by immunoblotting were transferred to PVDF membranes using the Pharmacia semi-dry electrotransfer system according to the manufacturers instructions. Serotype-specific antibodies used for detection of type A botulinal toxins and separated chains were produced in rabbits at the Food Research Institute and were conjugated to alkaline phosphatase. The antibodies did not cross react between type A neurotoxin and separated chains and ricin A chain. Antibodies specific to ricin A chain were purchased from Sigma Chemical Co. Alkaline phosphatase was detected using Sigma Fast nitro blue tetrazolium/bromochloro-indole phosphate tablets according to the manufacturers instructions (Sigma).

Toxin assays. Toxin titers were estimated in mice using the intraperitoneal method of Schantz and Kautter (1978) in 18–22 g, female, ICR strain mice. Chimeric toxins for titration were diluted as required in 30 mM sodium phosphate, 0.2% gelatin, pH 6.4 prior to injection into mice.

Chimeric toxin construction and purification. Separated type A botulinal heavy chain (6.75 mg) and ricin A chain (2.5 mg) were combined in a final volume of 20 ml and dialyzed in the case of the linker BMH against 50 mM sodium phosphate, 100 mM sodium chloride, 5 mM EDTA, 1 M urea, pH 7.0. The conjugation buffer for the linker DPDPB was identical except the pH was lowered to 6.0. After three changes of dialysis buffer over a period of seven hours at 4° C., linkers dissolved in DMSO were added at a final concentration of 1 mM. Linkage reactions were carried out in the dark at 4° C. for 16 hours (FIG. 4). Conjugation reactions were dialyzed against 50 mM sodium phosphate, pH 7.5. After three changes of buffer overnight at 4° C., the dialysate was clarified by centrifugation and the chimeric toxins applied at room temperature to separate 1.6×20 cm columns of Blue Sepharose (Pharmacia Biotechnology, Piscataway, N.J.) equilibrated in the same buffer (running buffer).

Loaded columns were washed with 20 column volumes of running buffer at which point the absorbance at 280 nm of the eluent was <0.01. Unbound reaction components including unreacted heavy chain, contaminating light chain, and reassociated botulinal heavy chain/light chain were removed from the column under these conditions. Bound reaction components including the chimeric toxin, monomeric and dimerized ricin A chain were eluted with a 0–0.5 M sodium chloride gradient in running buffer.

3. Results

Toxicity and western blotting results. Toxicity of the various reagent components as well as final conjugates are shown in Table 3.

TABLE 3

Toxicities of chimeric components including final chimeric toxins.[a]

| Rxn | Botulinal heavy chain | Ricin A chain | Unbound BlueSeph fracs | Bound BluSeph fracs |
|---|---|---|---|---|
| BMH | 100 | <5 | undetectable | 3000–6000 |
| DPDPB | 100 | <5 | undetectable | 33,000–66,000 |

[a]toxicities are expressed as mouse intraperitoneal $LD_{50}$/mg of protein.

Final yields for each reaction were 760 µg of DPDPB chimera and 616 µg of BMH chimera after the final purification step on BlueSepharose.

Western blots of chimeras separated on reduced and unreduced SDS-PAGE showed that unreduced chimeras (molecular weight approximately 130 kD) were reactive to both type A botulinum toxin-specific antibodies as well as ricin-specific antibodies. A very faint band at 160 kD representing two molecules of ricin per molecule of heavy chain was noted that was reactive to both types of antibodies. This band was estimated to represent <10% of the total amount of reactive protein per sample. Samples of the DPDPB chimera that had been reduced by the addition of 10 mM dithiothreitol prior to electrophoresis showed a band of ca. 100 kD that was reactive to type A botulinum toxin-specific antibodies but not ricin-specific antibodies. The same sample showed a band of ca. 33 kD that was reactive to ricin-specific antibodies but not botulinum-specific antibodies. These are the expected molecular masses of the botulinal H chain and ricin A chain, respectively. Both unreduced and reduced samples showed residual unreacted ricin A chain.

Unreduced samples of the BMH chimera subjected to SDS-PAGE, electroblotted to PVDF membrane, and treated with either antibody preparation showed a reactive band at ca. 130 kD the expected molecular mass of the designed chimera. Reduction of samples of this chimera with 10 mM dithiothreitol did not result in the appearance of a band at 100 kD reactive to botulinum-specific antibodies indicating that the chimera resulting from linkage with the BMH linker was not reducible as expected.

4. References

G. Ellman, "Tissue sulfhydryl groups," *Arch. Biochem. Biophys*. 82:70–77, 1959.

M. C. Goodnough and E. A. Johnson, "Stabilization of botulinum toxin type A during lyophilization," *Appl. Environ. Microbiol*. 58(10):3426–3428, 1992.

M. C. Goodnough and E. A. Johnson, "Recovery of type A botulinal toxin following lyophilization," In *Protein Formulations and Delivery*, J. Cleland and R. Langer, eds. American Chemical Society Press, 1994.

E. A. Johnson and M. C. Goodnough, "History, handling, and purification of botulinum toxin for medical use," In *Handbook of Dystonias*, J. Tsui, ed. Marcel Dekker Publishing, 1994.

V. Sathyamoorthy and B. DasGupta, "Separation, purification, partial characterization, and comparison of the heavy and light chains of botulinum neurotoxin types A, B, and E," *J. Biol. Chem*. 260:10461–10466.

G. Schiavo, et al., "An intact interchain disulfide bond is required for the neurotoxicity of tetanus toxin," *Infect. Immun*. 58:4136–4141, 1990.

E. Schantz and D. Kautter, "Standardized assay for *Clostridium botulinum* toxins," *J. Assoc. Off. Anal. Chem*. 61:96–99, 1978.

C. Tse, et al., "Preparation and characterization of homogeneous neurotoxin type A from *Clostridium botulinum*," *Eur. J. Biochem*. 122:493–500, 1982.

We claim:

1. A chimeric toxin comprising (a) a botulinal neurotoxin heavy chain; and (b) a non-clostridial toxin chain, wherein the chains are covalently connected with a covalent bond, the covalent bond comprises a reducible disulfide linker, and the toxicity of the toxin is at least $3.3 \times 10^4$ mouse intraperitoneal $LD_{50}$/mg of protein.

2. The toxin of claim 1 wherein the non-clostridial toxin is the ricin A chain.

3. The toxin of claim 2 wherein the botulinal neurotoxin heavy chain is botulinum neurotoxin type A heavy chain.

4. The toxin of claim 1 wherein the linker is 1,4-di-[3', 2'-pyridyditho-(propioamido)butane.

5. The toxin of claim 1 wherein the toxicity is at least $6.6 \times 10^4$ mouse intraperitoneal $LD_{50}$/mg of protein.

* * * * *

UNITED STATES PATENT AND TRADEMARK OFFICE
CERTIFICATE OF CORRECTION

PATENT NO. : 6,545,126 B1
DATED : April 8, 2003
INVENTOR(S) : Eric A. Johnson et al.

It is certified that error appears in the above-identified patent and that said Letters Patent is hereby corrected as shown below:

Column 2,
Line 39, "C. Botulinum Neurotoxin" should read -- C. botulinum Neurotoxin --.

Column 10,
Line 64, ">25" should read -- >5 --.

Column 12,
Line 63, "pyridydidtho-(propioamido" should read -- pyridyldithio-(propionamido) --.

Signed and Sealed this

Twenty-eighth Day of October, 2003

JAMES E. ROGAN
*Director of the United States Patent and Trademark Office*